(12) United States Patent
Huang et al.

(10) Patent No.: US 9,976,139 B2
(45) Date of Patent: *May 22, 2018

(54) RECOMBINANT DNA FOR GENE SUPPRESSION

(71) Applicant: MONSANTO TECHNOLOGY LLC, St. Louis, MO (US)

(72) Inventors: Shihshieh Huang, Woodland, CA (US); Thomas M. Malvar, N. Stonington, CT (US); Michael H. Luethy, Mystic, CT (US)

(73) Assignee: Monsanto Technology LLC, St. Louis, MO (US)

( * ) Notice: Subject to any disclaimer, the term of this patent is extended or adjusted under 35 U.S.C. 154(b) by 161 days.

This patent is subject to a terminal disclaimer.

(21) Appl. No.: 14/664,659

(22) Filed: Mar. 20, 2015

(65) Prior Publication Data

US 2015/0191728 A1 Jul. 9, 2015

Related U.S. Application Data

(63) Continuation of application No. 12/973,821, filed on Dec. 20, 2010, now Pat. No. 9,006,414, which is a continuation of application No. 11/057,062, filed on Feb. 10, 2005, now Pat. No. 7,855,323.

(60) Provisional application No. 60/543,157, filed on Feb. 10, 2004, provisional application No. 60/600,859, filed on Aug. 11, 2004, provisional application No. 60/543,187, filed on Feb. 10, 2004.

(51) Int. Cl.
| | |
|---|---|
| *C12N 15/113* | (2010.01) |
| *C12N 15/82* | (2006.01) |
| *C07H 21/02* | (2006.01) |
| *C12N 9/06* | (2006.01) |
| *C12N 15/11* | (2006.01) |
| *A61K 48/00* | (2006.01) |

(52) U.S. Cl.
CPC .......... *C12N 15/113* (2013.01); *C07H 21/02* (2013.01); *C12N 9/0028* (2013.01); *C12N 15/111* (2013.01); *C12N 15/8218* (2013.01); *C12N 15/8251* (2013.01); *C12N 15/8254* (2013.01); *A61K 48/00* (2013.01); *C12N 2310/11* (2013.01); *C12N 2310/111* (2013.01); *C12N 2310/14* (2013.01); *C12N 2310/53* (2013.01); *C12N 2330/30* (2013.01)

(58) Field of Classification Search
None
See application file for complete search history.

(56) References Cited

U.S. PATENT DOCUMENTS

| | | | |
|---|---|---|---|
| 5,082,993 A | 1/1992 | Strissel et al. | |
| 5,107,065 A | 4/1992 | Shewmaker et al. | |
| 5,231,020 A | 7/1993 | Jorgensen et al. | |
| 5,258,300 A | 11/1993 | Glassman et al. | |
| 5,283,184 A | 2/1994 | Jorgensen et al. | |
| 5,508,468 A | 4/1996 | Lundquist et al. | |
| 5,545,545 A | 8/1996 | Gengenbach et al. | |
| 5,759,829 A | 6/1998 | Shewmaker et al. | |
| 5,773,691 A | 6/1998 | Falco et al. | |
| 6,054,299 A | 4/2000 | Conrad | |
| 6,054,439 A | 4/2000 | Szyf et al. | |
| 6,090,627 A | 7/2000 | Kemp et al. | |
| 6,160,208 A | 12/2000 | Lundquist et al. | |
| 6,326,193 B1 | 12/2001 | Liu et al. | |
| 6,326,527 B1 | 12/2001 | Kirihara et al. | |
| 6,329,574 B1 | 12/2001 | Lundquist et al. | |
| 6,433,252 B1 | 8/2002 | Kriz et al. | |
| 6,459,019 B1 | 10/2002 | Falco et al. | |
| 6,506,559 B1 | 1/2003 | Fire et al. | |
| 6,635,806 B1 | 10/2003 | Kriz et al. | |
| 6,777,589 B1 | 8/2004 | Lundquist et al. | |
| 6,825,400 B2 | 11/2004 | Behr et al. | |
| 6,858,778 B1 | 2/2005 | Jung et al. | |
| 7,071,383 B2 | 7/2006 | Falco | |
| 7,105,591 B2 | 9/2006 | Weber | |
| 7,109,393 B2 | 9/2006 | Gutterson et al. | |
| 7,157,281 B2 | 1/2007 | Dizigan et al. | |
| 7,683,237 B2 | 3/2010 | Kriz et al. | |
| 7,855,323 B2 * | 12/2010 | Huang ................... | C07H 21/02 435/320.1 |
| 9,006,414 B2 * | 4/2015 | Huang ................... | C07H 21/02 435/320.1 |
| 2002/0048814 A1 | 4/2002 | Oeller | |
| 2003/0036197 A1 | 2/2003 | Glassman et al. | |

(Continued)

FOREIGN PATENT DOCUMENTS

| | | |
|---|---|---|
| EP | 0 426 195 | 5/1991 |
| EP | 0 428 881 A1 | 5/1991 |

(Continued)

OTHER PUBLICATIONS

Thomas et al, 2001, Plant J., 25:417-425.*
Khlare et al, 2002, PNAS, 99:11981-11986.*
McManus et al, 2002, RNA, 8:842-850.*
Alvarez et al., "Crabs Claw and Spatula, two *Arabidopsis* genes that control carpel development in parallel with Agamous," *Development*, 126:2377-2386, 1999.
Arruda et al., "Regulation of lysine catabolism in higher plants," *Trends in Plant Sci.*, 5(8):324-330, 2000.
Bagga et al., "Coexpression of the maize δ-zein and β-zein genes results in stable accumulation of δ-zein in endoplasmic reticulum-derived protein bodies formed by β-zein," *Plant Cell*, 9:1683-1696, 1997.

(Continued)

*Primary Examiner* — Jason Deveau Rosen
(74) *Attorney, Agent, or Firm* — Dentons US LLP; Amanda Carmany-Rampey

(57) ABSTRACT

Anti-sense-oriented RNA gene suppression agents in the form of a loop of anti-sense-oriented RNA is produced in cells of transgenic organisms, e.g. plants, by transcription from a recombinant DNA construct which comprises in 5' to 3' order a promoter element operably linked to an anti-sense-oriented DNA element and a complementary DNA element.

11 Claims, 3 Drawing Sheets

(56) References Cited

U.S. PATENT DOCUMENTS

| | | |
|---|---|---|
| 2003/0074684 A1 | 4/2003 | Graham et al. |
| 2003/0175965 A1 | 9/2003 | Lowe et al. |
| 2004/0029283 A1 | 2/2004 | Fillatti |
| 2005/0193444 A1 | 9/2005 | Malvar et al. |
| 2005/0255568 A1 | 11/2005 | Bailey et al. |
| 2005/0260754 A1 | 11/2005 | Kock et al. |
| 2006/0075515 A1 | 4/2006 | Luethy et al. |
| 2009/0188005 A1 | 7/2009 | Boukharov et al. |
| 2010/0122381 A1 | 5/2010 | Buehler et al. |
| 2011/0113514 A1 | 5/2011 | Malvar et al. |

FOREIGN PATENT DOCUMENTS

| | | |
|---|---|---|
| JP | A-7-504892 | 7/1995 |
| WO | WO 93/15088 | 8/1993 |
| WO | WO 93/19190 A1 | 9/1993 |
| WO | WO 95/15392 A1 | 6/1995 |
| WO | WO 98/26064 A2 | 6/1998 |
| WO | WO 98/42831 A2 | 10/1998 |
| WO | WO 98/53083 A1 | 11/1998 |
| WO | WO 99/49029 A1 | 9/1999 |
| WO | WO 99/53050 A1 | 10/1999 |
| WO | WO 99/61631 | 12/1999 |
| WO | WO 2003/077643 A2 | 9/2003 |
| WO | WO 2003/078629 A1 | 9/2003 |
| WO | WO 2005/077116 A2 | 8/2005 |
| WO | WO 2005/077117 A2 | 8/2005 |
| WO | WO 2006/073727 A2 | 7/2006 |
| WO | WO 2006/099249 A2 | 9/2006 |
| WO | WO 2007/024207 A1 | 3/2007 |

OTHER PUBLICATIONS

Bonnassie et al., "Nucleotide sequence of the dapA gene from corynebacterium glutamicum," *Nucleic Acids Res.*, 18:6421, 1990.

Chuang et al., "Specific and heritable genetic interference by double-stranded RNA in *Arabidopsis thaliana*", *PNAS*, 97:4985-4990, Apr. 2000.

Chuang et al., "The Perianthia gene encodes a bZIP protein involved in the determination of floral organ number in *Arabidopsis thaliana*," *Genes & Devel.*, 13:334-344, 1999.

Debuck et al., "Transgene silencing of invertedly repeated transgenes is released upon deletion of one of the transgenes involved", *Plant Mol. Biol.*, 46(4):433-445, Jul. 2001.

Falco et al., "Transgenic canola and soybean seeds with increased lysine," *Biotechnology*, 13(6):582, 1995.

Final Assessment Report of Application A549, Food Derived from High Lysine Corn LY038, *Food Standards of Australia and New Zealand*, http:--cera-gmc.org-docs-decdocs-07-219-001.pdf, 2006.

Frizzi et al., "Modifying lysine biosynthesis and catabolism in corn with a single bifunctional expression-silencing transgene," *Plant Biotechnology*, 6:13-21, 2008.

Gaziola et al., "Quality protein maize: a biochemical study of enzymes involved in lysine metabolism," *J. Agric. Food Chem.*, 47:1268-1275, 1999.

Helliwell et al., "High-throughput vectors for efficient gene silencing in plants ," *Funct. Plant Biol.*, 29:1217-1225, 2002.

Houmard et al., "High-lysine corn generated by endosperm-specific suppression of lysine catabolism using RNAi," *Plant Biotechnology J.*, 5:605-614, 2007.

Huang et al., "High-lysine corn produced by the combination of enhanced lysine biosynthesis and reduced zein accumulation," *Plant Biotechnology Journal*, 3:555-569, 2005.

Huang et al., "Improving nutritional quality of maize proteins by expressing sense and antisense zein genes," *J. Agric. Food Chem.*, 52:1958-1964, 2004.

Huang et al.,"High lysine and high tryptophan transgenic maize resulting from the reduction of both 19-and 22-kD alpha-zeins," Plant Molecular Biology, 61(3):525-535, 2006.

Jorgensen et al., "TDNA is organized predominantly in inverted repeat structures in plants transformed with Agrobacterium tumefaciens C58 derivatives", *Mol. Gen. Genet.*, 207:471-477, 1987.

Kemper et al., "The role of opaque2 in the control of lysine-degrading activities in developing maize endosperm," *Plant Cell*, 11:1981-1993, 1999.

Klahre et al., "High Molecular weight RNAs and small interfering RNAs induce systemic posttranscriptional gene silencing in plants," *PNAS* 99:11981-11986; 2002.

Mette et al., "Production of aberrant promoter transcripts contributes to methylation and silencing of unlinked homologous promoters intrans", *The EMBO Journal*, 18(1):241-248, Jan. 1999.

Mette et al., "Transcriptional silencing and promoter methylation triggered by double-stranded RNA", *The EMBO Journal*, 19(19):5194-5201, Oct. 2000.

Paul et al., "Effective expression of small interfering RNA in human cells," *Nature Biotechnol.* 29:505-508, 2002.

Rebowski et al., "Antisense hairpin loop oligonucleotides as inhibitors of expression of multidrug resistance-associated protein 1: their stability in fetal calf serum and human plasma," ACTA Biochimica Polonica, 48(4):1061-1076, 2001.

Redenbaugh et al., "Aminoglycoside 3'-phosphototransferase-II (APH) (3')II)—review of its safety and use in the production of genetically-engineered plants," *Food Biotechnology*, 8(2-3):137-165, 1994.

Redenbaugh et al., "Determination of the safety of genetically engineered crops," ACS Symposium Series 605:72-87, 1995.

Redenbaugh et al., "Regulatory assessment of the flavr-savr tomato," *Trends in Food Science & Technology*, 5(4):105-110, 1994.

Redenbaugh et al., "Regulatory issues for commercialization of tomatoes with an antisense polygalacturonase gene," *In Vitro Cellular & Developmental Biology—Plant*, 29P(1):17-26, 1993.

Redenbaugh et al., "Safety assessment of genetically engineered flave savr TM tomato", CRC Press, Inc, pp. 88-102, 1992.

Reyes et al., "Genetic manipulation of lysine catabolism in maize kernels," *Plant Mol. Biol.*, 69:81-89, 2009.

Richaud et al., "Chromosomal location and nucleotide sequence of the *Escherichia coli* dapA gene," *J. of Bacteriol.*, 166(1):297-300, 1986.

Russell et al., "Tissue-specific expression in transgenic maize of four endosperm promoters from maize and riceZein Z27," *Transgenic Res.*, 6(2):157-168, 1997.

Sanders et al., "Tomato transgene structure and silencing", *Nature Biotechnology*, 23(3):287-289, Mar. 2005.

Satterfield et al., "What does ppm or ppb mean," *On Tap* pp. 38-40, Fall 2004.

Segai et al., "A new opaque variant of maize by a single dominant RNA-interference-inducing transgene," *Genetics*, 165:387-397, 2003.

Shaul et al., "Increased lysine synthesis in tobacco plants that express high levels of bacterial dihydrodipicolinate synthase in their chloroplasts," *The Plant Journal*, 2(2):203-209, 1992.

Sijen et al., "RNA-mediated virus resistance: Role of repeated transgenes and delineation of targeted regions", *The Plant Cell*, 8:2277-2294, Dec. 1996.

Singer et al., "Genes & Genomes: A Changing Perspective," University Science Books, pp. 733-740, 1991.

Smith et al., "Gene expression—total silencing by intron-spliced hairpin RNAs," *Nature*, 407:319-320, 2000.

Stam et al, "Post-transcriptional silencing of endogenous genes in Petunia by inverted transgene repeats", *The Plant Journal*, 12:63-82, 1997.

Thomas et al., "Size constraints for targeting post-transcriptional gene silencing and for RNA-directed methylation in *Nicotiana benthamiana* using a potato virus X vector," *Plant J.* 25:417-425; 2001.

Supplemental European Search Report dated Jul. 21, 2008.

Unger et al., "Dominant negative mutants of opaque2 suppress transactivation of a 22-kD zein promoter by opaque2 in maize endosperm cells," *The Plant Cell*, 5:831-841, 1993.

Wang et al., "Genetic analysis of amino acid accumulation in opaque-2 maize endosperm," *Plant Physiol.*, 125:1766-1777, 2001.

Waterhouse et al., "Virus Resistance and gene silencing in plants can be induced by simultaneous expression of sense and antisense RNA", *PNAS*, 95(23):13959-64, Nov. 1998.

(56) References Cited

OTHER PUBLICATIONS

Wesley et al., "Construct design for efficient, effective and high-throughput gene silencing in plants," *Plant J.*, 27(6):581-590, 2001.
Wu et al., "Quantitative nature of the prolamin-box, ACGT and AACA motifs in a rice glutelin gene promoter: minimal cis-element requirements for endosperm-specific gene expression," *Plant J.*, 23(3):415-421, 2000.
Yu et al., "RNA interference by expression of short-interfering RNAs and hairpin RNAs in mammalian cells," *PNAS* 99:6047-6052, 2002.
Zhu et al., "A T-DNA insertion knockout of the bifunctional lysine-ketoglutarate reductase-saccharopine dehydrogenase gene elevates lysine levels in *Arabidopsis* seeds," *Plant Physiology*, 126:1539-1545, 2001.
Zhu et al., "Increased lysine synthesis coupled with a knockout of its catabolism synergistically boosts lysine content and also transregulates the metabolism of other amino acids in *Arabidopsis* seeds," *Plant Cell*, 15:845-853, 2003.
Office Action regarding U.S. Appl. No. 11/202,401, dated Feb. 21, 2008.
Amendment and Response to Office Action regarding U.S. Appl. No. 11/202,401, dated Jun. 23, 2008.
Office Action regarding U.S. Appl. No. 11/202,401, dated Sep. 30, 2008.

\* cited by examiner

RECOMBINANT DNA FOR GENE SUPPRESSION

CROSS REFERENCE TO RELATED APPLICATIONS

This application is a continuation of U.S. application Ser. No. 12/973,821 filed Dec. 20, 2010, which application is a continuation of U.S. application Ser. No. 11/057,062 filed Feb. 10, 2005, now U.S. Pat. No. 7,855,323, issued Dec. 21, 2010, which application claims priority under 35 USC § 119(e) to provisional application Ser. No. 60/543,157, filed Feb. 10, 2004, No. 60/543,187 filed Feb. 10, 2004 and No. 60/600,859, filed Aug. 11, 2004, the disclosures of all of which are incorporated by reference in their entireties.

INCORPORATION OF SEQUENCE LISTING

A computer readable form of the sequence listing is contained in the file named "53428B.ST25.txt" which is 21 kb (measured in MS-Windows) and was created on Feb. 9, 2005 and is located on a CDROM, which is filed herewith and herein incorporated by reference.

FIELD OF THE INVENTION

Disclosed herein are seeds for transgenic corn having elevated amino acid level, recombinant DNA constructs for producing gene-suppressing loops of anti-sense RNA and methods of making and using such constructs and transgenic plants expressing gene-suppressing loops of anti-sense RNA.

BACKGROUND

Certain plants have low levels of specific amino acids compared to other plants, e.g. corn has low levels of lysine, methionine and tryptophan. Efforts to increase amino acid levels in transgenic plants include expressing recombinant DNA which encodes proteins in an amino acid synthesis pathway at higher levels than native genes. One such gene for producing enhanced levels of lysine in corn is a bacterial dihydropicolinic acid synthase. A concept for even more enhanced levels of amino acids includes suppression of genes encoding proteins in amino acid catabolic pathways.

Gene suppression includes any of the well-known methods for suppressing transcription of a gene or the accumulation of the mRNA corresponding to that gene thereby preventing translation of the transcript into protein. More particularly, gene suppression mediated by inserting a recombinant DNA construct with anti-sense oriented DNA to regulate gene expression in plant cells is disclosed in U.S. Pat. No. 5,107,065 (Shewmaker et al.) and U.S. Pat. No. 5,759,829 (Shewmaker et al.). Plants transformed using such anti-sense oriented DNA constructs for gene suppression can comprise integrated DNA arranged as an inverted repeat that resulted from co-insertion of several copies of the transfer DNA (T-DNA) into plants by Agrobacterium-mediated transformation, as disclosed by Redenbaugh et al. in "Safety Assessment of Genetically Engineered Flavr Savr™ Tomato, CRC Press, Inc. (1992). Inverted repeat insertions can comprise a part or all of the T-DNA, e.g. contain an inverted repeat of a complete or partial anti-sense construct. Screening for inserted DNA comprising inverted repeat elements can improve the efficiency of identifying transformation events effective for gene silencing when the transformation construct is a simple anti-sense DNA construct.

Gene suppression triggered by inserting a recombinant DNA construct with sense-oriented DNA to regulate gene expression in plants is disclosed in U.S. Pat. No. 5,283,184 (Jorgensen et al.) and U.S. Pat. No. 5,231,020 (Jorgensen et al.). Inserted T-DNA providing gene suppression in plants transformed with such sense constructs by Agrobacterium is organized predominately in inverted repeat structures, as disclosed by Jorgensen et al., Mol. Gen. Genet., 207: 471-477 (1987). See also Stam et al., The Plant Journal, 12: 63-82 (1997) and De Buck et al., Plant Mol. Biol. 46 433-445 (2001), who used segregation studies to support Jorgensen's finding that in many events gene silencing is mediated by multimeric transgene T-DNA where the T-DNAs are arranged in inverted repeats. Screening for inserted DNA comprising inverted repeat elements can improve the gene silencing efficiency when transforming with simple sense-orientated DNA constructs.

Gene silencing can also be effected by transcribing RNA from both a sense and an anti-sense oriented DNA using two separate transcription units, e.g. as disclosed by Shewmaker et al. in U.S. Pat. No. 5,107,065 where in Example 1 a binary vector was prepared with both sense and anti-sense aroA genes. Similar constructs are disclosed in International Publication No. WO 99/53050 (Waterhouse et al.). See also U.S. Pat. No. 6,326,193 where gene targeted DNA is operably linked to opposing promoters.

Gene suppression can be achieved in plants by providing transformation constructs that are capable of generating an RNA that can form double-stranded RNA along at least part of its length. Gene suppression in plants is disclosed in EP 0426195 A1 (Goldbach et al.) where recombinant DNA constructs for transcription into hairpin RNA provided transgenic plants with resistance to tobacco spotted wilt virus. See also Sijen et al., The Plant Cell, Vol. 8, 2277-2294 (1996) which discloses the use of constructs carrying inverted repeats (sense followed by anti-sense) of a cowpea mosaic virus gene in transgenic plants to mediate virus resistance. See also International Publication No. 98/53083 (Grierson et al.) and related U.S. Patent Application Publication No. 2003/0175965 A1 (Lowe et al.) which disclose gene suppression, using a double stranded RNA construct comprising a gene coding sequence preceded by an inverted repeat of 5'UTR. Constructs for posttranscriptional gene suppression in plants by double-stranded RNA of the target gene are also disclosed in International Publication No. WO 99/53050 (Waterhouse et al.) and International Publication No. WO 99/49029 (Graham et al.). See also U.S. Patent Application Publication No. 2002/0048814 A1 (Oeller) where DNA constructs are transcribed to sense or anti-sense RNA with a hairpin-forming poly(T)-poly(A) tail. See also U.S. Patent Application Publication No. 2003/0018993 A1 (Gutterson et al.) where sense or anti-sense DNA is followed by an inverted repeat of the 3' untranslated region of the NOS gene. See also U.S. Patent Application Publication No. 2003/0036197 A1 (Glassman et al.) where RNA for reducing the expression of target mRNA comprises a part with homology to target mRNA and a part with complementary RNA regions that are unrelated to endogenous RNA.

The production of dsRNA in plants to inhibit gene expression, e.g. in a nematode feeding on the plant, is disclosed U.S. Pat. No. 6,506,559 (Fire et al.). Multi-gene suppression vectors for use in plants are disclosed in U.S. patent application Ser. No. 10/465,800 (Fillatti).

Transcriptional suppression such as promoter trans suppression can be affected by a expressing a DNA construct comprising a promoter operably linked to inverted repeats of promoter DNA from a target gene. Constructs useful for such gene suppression mediated by promoter trans suppression are disclosed by Mette et al., The EMBO Journal, Vol. 18, pp. 241-148, (1999) and by Mette et al., The EMBO Journal, Vol. 19, pp. 5194-5201-148, (2000), both of which are incorporated herein by reference.

All of the above-described patents, applications and international publications disclosing materials and methods for gene suppression in plants are incorporated herein by reference.

SUMMARY OF THE INVENTION

This invention provides methods and recombinant DNA constructs useful for producing anti-sense-oriented RNA for gene suppression in transgenic organisms. In one aspect of the invention recombinant DNA constructs comprise in 5' to 3' order a promoter element operably linked to an anti-sense-oriented DNA element and a sense-oriented DNA element, where the sense-oriented DNA element is shorter than the anti-sense-oriented DNA element, and sense-oriented RNA transcribed by the sense-oriented DNA is complementary to the 5'-most end of anti-sense-oriented RNA transcribed by the anti-sense-oriented DNA element, wherein said transcribed RNA forms a into a loop of anti-sense-oriented RNA for suppressing said at least one target gene.

The sense-oriented DNA can be cloned as an inverted repeat of 5'-most segment of the anti-sense-oriented DNA element. Constructs with such sense-oriented DNA are transcribed to RNA that forms a loop of anti-sense-oriented RNA closed at its ends with a double-stranded RNA (dsRNA) segment, e.g. as illustrated in FIG. 1. To form an anti-sense-oriented RNA loop the complementary DNA element is conveniently not more than about one-half the length of the anti-sense-oriented DNA element, often not more than one-third the length of said anti-sense-oriented DNA element, e.g. not more than one-quarter the length of said anti-sense-oriented DNA element. The overall lengths of the combined DNA elements can vary. For instance, the anti-sense-oriented DNA element can consist of from 500 to 5000 nucleotides and the complementary DNA element can consist of from 50 to 500 nucleotides. In many cases it is useful for the anti-sense-oriented DNA segment to be more than twice the length of the sense-oriented DNA segment to allow for formation of an anti-sense-oriented RNA loop.

The anti-sense transcription unit can be designed to suppress multiple genes where the DNA is arranged with two or more anti-sense-oriented elements from different genes targeted for suppression followed by a complementary sense-oriented element, e.g. complementary to at least a part of the 5' most anti-sense element.

Aspects of this invention provide methods of suppressing the expression of a gene by providing in the cells of a plant a gene-suppressing, recombinant DNA construct of this invention that transcribes to an anti-sense loop of RNA. In other aspects of the invention, e.g. for providing traits other than plants with enhanced amino acid, the gene targeted for suppression can be a plant gene, a plant pest gene or a plant pathogen gene or a combination thereof. In constructs, methods and plants of this invention the gene targeted for silencing can be a native gene or an exogenous gene or a gene in an organism that ingests or contacts plant tissue including cells comprising anti-sense RNA in a loop. Plant pathogens include viruses such a cucumber mosaic virus; plant pests include nematodes such as soybean cyst nematode and root knot nematode, insect larvae such a lepidopteran larvae, sucking insects such as aphids and leaf eating insects such as locust.

DETAILED DESCRIPTION

Figure 1:
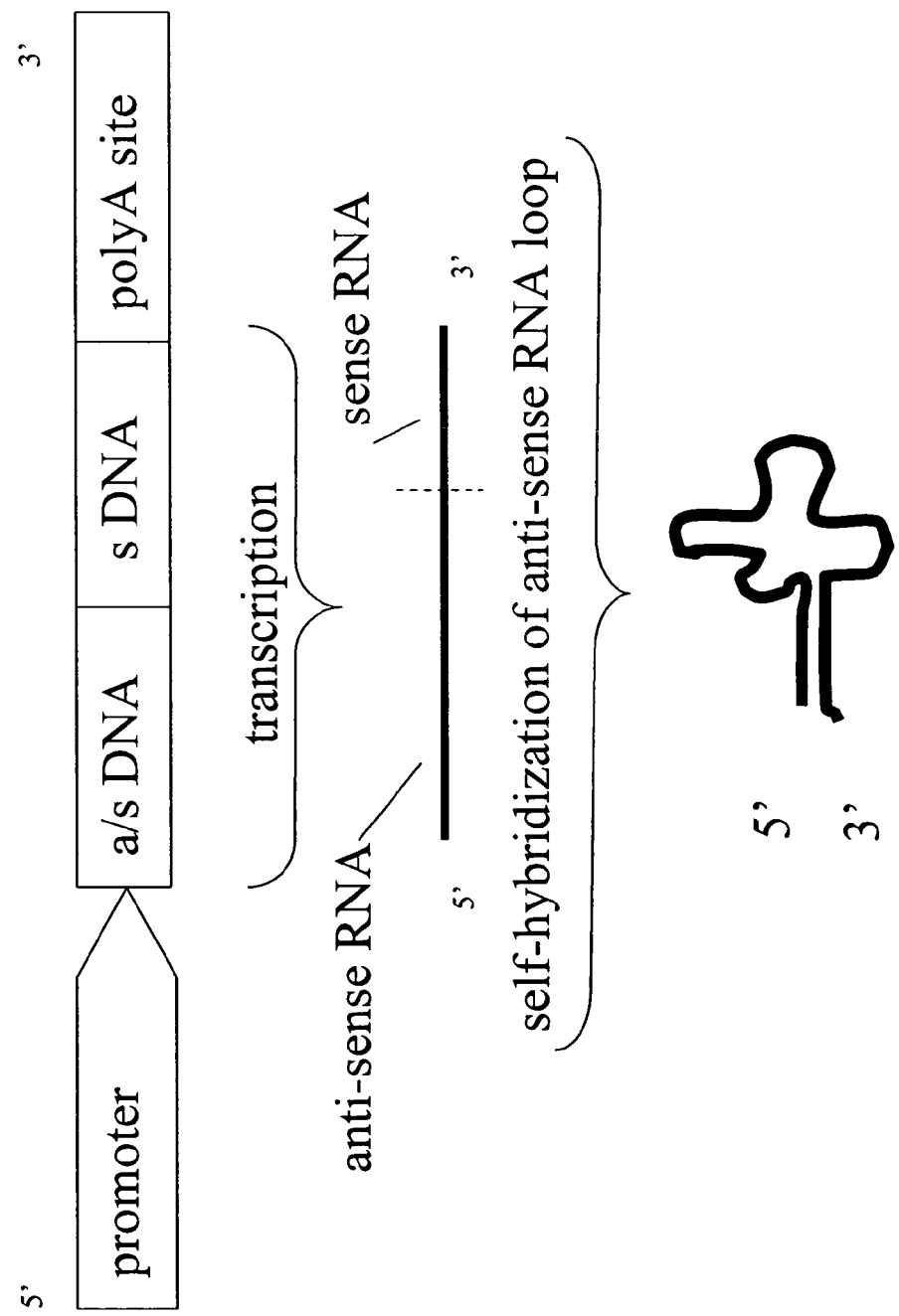
FIG. 1 is a schematic illustration of a recombinant DNA construct useful in this invention to produce an anti-sense-oriented loop of RNA.

SEQ ID NO:1 and SEQ ID NO:2 are nucleotide sequences of recombinant DNA constructs useful for transcribing RNA that can form an anti-sense-oriented RNA loop for suppressing one or multiple genes in transgenic plants. See Tables 1 and 2 for a description of elements of those constructs.

As used herein, "complementary" refers to polynucleotides that are capable of hybridizing, e.g. sense and anti-sense strands of DNA or self-complementary strands of RNA, due to complementarity of aligned nucleotides permitting C-G and A-T or A-U bonding.

As used herein "vector" means a DNA molecule capable of replication in a host cell and/or to which another DNA segment can be operatively linked so as to bring about replication of the attached segment. A plasmid is an exemplary vector.

As used herein a "transgenic" organism, e.g. plant or seed, is one whose genome has been altered by the incorporation of recombinant DNA comprising exogenous genetic material or additional copies of native genetic material, e.g. by transformation or recombination of the organism or an ancestral organism. Transgenic plants include progeny plants of an original plant derived from a transformation process including progeny of breeding transgenic plants with wild type plants or other transgenic plants. Crop plants of particular interest in the present invention include, but are not limited to maize, soybean, cotton, canola (rape), wheat, rice, sunflower, safflower and flax. Other crops of interest include plants producing vegetables, fruit, grass and wood.

Recombinant DNA Constructs for Plant Transformation

Recombinant DNA constructs for producing looped, anti-sense RNA, gene suppression agents in transgenic plants can be readily prepared by those skilled in the art. Typically, such a DNA construct comprises as a minimum a promoter active in the tissue targeted for suppression, a transcribable DNA element having a sequence that is complementary to nucleotide sequence of a gene targeted for suppression and a transcription terminator element. The targeted gene element copied for use in transcribable DNA in the gene suppression construct can be a promoter element, an intron element, an exon element, a 5' UTR element, or a 3'UTR element. Although the minimum size of DNA copied from sequence of a gene targeted for suppression is believed to be about 21 or 23 nucleotides; larger nucleotide segments are preferred, e.g. up the full length of a targeted gene. Useful lengths of either DNA segment are in the range of 50 to 5000 nucleotides, say anti-sense-oriented DNA of 500 to 5000 nucleotides in length and complementary DNA elements can be 50 to 500 or more nucleotides in length. The DNA element can comprise multiple parts of a gene, e.g. nucleotides that are complementary to contiguous or separated gene elements of UTR, exon and intron. Such constructs may also comprise other regulatory elements, DNA encoding transit peptides, signal peptides, selective markers and screenable markers as desired.

With reference to FIG. 1 there is schematically shown a recombinant DNA construct comprising a promoter element, an anti-sense-oriented DNA element (denoted "a/s DNA"), a complementary sense-oriented DNA element (denoted "s DNA") and DNA providing polyadenylation signals and site (denoted "polyA site"). The DNA construct is transcribed to RNA comprising an anti-sense-oriented RNA segment and a complementary RNA segment which is complementary to the 5'-most end of the anti-sense-oriented RNA segment. The 5' and 3' ends of the anti-sense RNA can self hybridize to form a double-stranded RNA segment that closes a loop of anti-sense-oriented RNA. For example, if the nucleotide sequence of the 5'-most end of the strand of transcribed anti-sense-oriented DNA is 5'-CGGCATA-, the sequence of the 3'-most end of the transcribed strand of the inverted repeat DNA will be -TATGCCG-3' which is readily cloned from the source DNA providing the anti-sense element. With such sequences the loop of anti-sense-oriented RNA will extend from one side of a dsRNA segment, e.g.

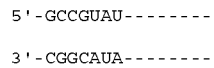

The anti-sense-oriented DNA and its self-complementary DNA can be contiguous or separated by vector DNA, e.g. up to about 100 nucleotides or so of vector DNA separating restriction sites used for vector assembly.

Recombinant DNA constructs can be assembled using commercially available materials and methods known to those of ordinary skill in the art. A useful technology for building DNA constructs and vectors for transformation is the GATEWAY™ cloning technology (available from Invitrogen Life Technologies, Carlsbad, Calif.) uses the site specific recombinase LR cloning reaction of the Integrase att system from bacteriophage lambda vector construction, instead of restriction endonucleases and ligases. The LR cloning reaction is disclosed in U.S. Pat. Nos. 5,888,732 and 6,277,608, U.S. Patent Application Publications 2001283529, 2001282319 and 20020007051, all of which are incorporated herein by reference. The GATEWAY™ Cloning Technology Instruction Manual which is also supplied by Invitrogen also provides concise directions for routine cloning of any desired DNA into a vector comprising operable plant expression elements.

An alternative vector fabrication method employs ligation-independent cloning as disclosed by Aslanidis, C. et al., Nucleic Acids Res., 18, 6069-6074, 1990 and Rashtchian, A. et al., Biochem., 206, 91-97, 1992 where a DNA fragment with single-stranded 5' and 3' ends are ligated into a desired vector which can then be amplified in vivo.

Numerous promoters that are active in plant cells have been described in the literature. These include promoters present in plant genomes as well as promoters from other sources, including nopaline synthase (nos) promoter and octopine synthase (ocs) promoters carried on tumor-inducing plasmids of Agrobacterium tumefaciens, caulimovirus promoters such as the cauliflower mosaic virus or figwort mosaic virus promoters. For instance, see U.S. Pat. Nos. 5,322,938 and 5,858,742 which disclose versions of the constitutive promoter derived from cauliflower mosaic virus (CaMV35S), U.S. Pat. No. 5,378,619 which discloses a Figwort Mosaic Virus (FMV) 35S promoter, U.S. Pat. No. 5,420,034 which discloses a napin promoter, U.S. Pat. No. 6,437,217 which discloses a maize RS81 promoter, U.S. Pat. No. 5,641,876 which discloses a rice actin promoter, U.S. Pat. No. 6,426,446 which discloses a maize RS324 promoter, U.S. Pat. No. 6,429,362 which discloses a maize PR-1 promoter, U.S. Pat. No. 6,232,526 which discloses a maize A3 promoter, U.S. Pat. No. 6,177,611 which discloses constitutive maize promoters, U.S. Pat. No. 6,433,252 which discloses a maize L3 oleosin promoter, U.S. Pat. No. 6,429,357 which discloses a rice actin 2 promoter and intron, U.S. Pat. No. 5,837,848 which discloses a root specific promoter, U.S. Pat. No. 6,084,089 which discloses cold inducible promoters, U.S. Pat. No. 6,294,714 which discloses light inducible promoters, U.S. Pat. No. 6,140,078 which discloses salt inducible promoters, U.S. Pat. No. 6,252,138 which discloses pathogen inducible promoters, U.S. Pat. No. 6,175,060 which discloses phosphorus deficiency inducible promoters, U.S. Pat. No. 6,635,806 which discloses a coixin promoter, U.S. 2002/0192813A1 which discloses 5', 3' and intron elements useful in the design of effective plant expression vectors, U.S.2004/0216189 A1 which discloses a maize chloroplast aldolase promoter, and U.S. 2004/0123347A1 which discloses water-deficit inducible promoters, all of which are incorporated herein by reference. These and numerous other promoters that function in plant cells are known to those skilled in the art and available for use in recombinant polynucleotides of the present invention to provide for expression of desired genes in transgenic plant cells.

Furthermore, the promoters may be altered to contain multiple "enhancer sequences" to assist in elevating gene expression. Such enhancers are known in the art. By including an enhancer sequence with such constructs, the expression of the selected protein may be enhanced. These enhancers often are found 5' to the start of transcription in a promoter that functions in eukaryotic cells, but can often be inserted upstream (5') or downstream (3') to the coding sequence. In some instances, these 5' enhancing elements are introns. Particularly useful as enhancers are the 5' introns of the rice actin 1 (see U.S. Pat. No. 5,641,876) and rice actin 2 genes, the maize alcohol dehydrogenase gene intron, the maize heat shock protein 70 gene intron (U.S. Pat. No. 5,593,874) and the maize shrunken 1 gene.

In other aspects of the invention, sufficient expression in plant seed tissues is desired to effect improvements in seed composition. Exemplary promoters for use for seed composition modification include promoters from seed genes such as napin (U.S. Pat. No. 5,420,034), maize L3 oleosin (U.S. Pat. No. 6,433,252), zein Z27 (Russell et al. (1997) Transgenic Res. 6(2):157-166), globulin 1 (Belanger et al (1991) Genetics 129:863-872), glutelin 1 (Russell (1997) supra), and peroxiredoxin antioxidant (Per1) (Stacy et al. (1996) Plant Mol Biol. 31(6):1205-1216).

Recombinant DNA constructs prepared in accordance with the invention will often include a 3' element that typically contains a polyadenylation signal and site, especially if the recombinant DNA is intended for protein expression as well as gene suppression. Well-known 3' elements include those from Agrobacterium tumefaciens genes such as nos 3', tml 3', tmr 3', tms 3', ocs 3', tr7 3', e.g. disclosed in U.S. Pat. No. 6,090,627, incorporated herein by reference; 3' elements from plant genes such as wheat (Triticum aesevitum) heat shock protein 17 (Hsp17 3'), a wheat ubiquitin gene, a wheat fructose-1,6-biphosphatase gene, a rice glutelin gene a rice lactate dehydrogenase gene and a rice beta-tubulin gene, all of which are disclosed in U.S. published patent application 2002/0192813 A1, incorporated herein by reference; and the pea (*Pisum sativum*) ribulose biphosphate carboxylase gene (rbs 3), and 3' elements from the genes within the host plant.

The gene-suppressing recombinant DNA constructs can also be stacked with DNA imparting other traits of agronomic interest including DNA providing herbicide resistance or insect resistance such as using a gene from *Bacillus thuringensis* to provide resistance against lepidopteran, coliopteran, homopteran, hemiopteran, and other insects. Herbicides for which resistance is useful in a plant include glyphosate herbicides, phosphinothricin herbicides, oxynil herbicides, imidazolinone herbicides, dinitroaniline herbicides, pyridine herbicides, sulfonylurea herbicides, bialaphos herbicides, sulfonamide herbicides and glufosinate herbicides. Persons of ordinary skill in the art are enabled in providing stacked traits by reference to U.S. patent application publications 2003/0106096A1 and 2002/0112260A1 and U.S. Pat. Nos. 5,034,322; 5,776,760; 6,107,549 and 6,376,754 and to insect/nematode/virus resistance by reference to U.S. Pat. Nos. 5,250,515; 5,880,275; 6,506,599; 5,986,175 and U.S. Patent Application Publication 2003/0150017 A1, all of which are incorporated herein by reference.

Transformation Methods—

Numerous methods for transforming plant cells with recombinant DNA are known in the art and may be used in the present invention. Two commonly used methods for plant transformation are *Agrobacterium*-mediated transformation and microprojectile bombardment. Microprojectile bombardment methods are illustrated in U.S. Pat. No. 5,015,580 (soybean); U.S. Pat. No. 5,550,318 (corn); U.S. Pat. No. 5,538,880 (corn); U.S. Pat. No. 5,914,451 (soybean); U.S. Pat. No. 6,160,208 (corn); U.S. Pat. No. 6,399,861 (corn) and U.S. Pat. No. 6,153,812 (wheat) and *Agrobacterium*-mediated transformation is described in U.S. Pat. No. 5,159,135 (cotton); U.S. Pat. No. 5,824,877 (soybean); U.S. Pat. No. 5,591,616 (corn); and U.S. Pat. No. 6,384,301 (soybean), all of which are incorporated herein by reference. For *Agrobacterium tumefaciens* based plant transformation system, additional elements present on transformation constructs will include T-DNA left and right border sequences to facilitate incorporation of the recombinant polynucleotide into the plant genome.

In general it is useful to introduce recombinant DNA randomly, i.e. at a non-specific location, in the genome of a target plant line. In special cases it may be useful to target recombinant DNA insertion in order to achieve site-specific integration, e.g. to replace an existing gene in the genome, to use an existing promoter in the plant genome, or to insert a recombinant polynucleotide at a predetermined site known to be active for gene expression. Several site specific recombination systems exist which are known to function implants include cre-lox as disclosed in U.S. Pat. No. 4,959,317 and FLP-FRT as disclosed in U.S. Pat. No. 5,527,695, both incorporated herein by reference.

Transformation methods of this invention are preferably practiced in tissue culture on media and in a controlled environment. "Media" refers to the numerous nutrient mixtures that are used to grow cells in vitro, that is, outside of the intact living organism. Recipient cell targets include, but are not limited to, meristem cells, callus, immature embryos and gametic cells such as microspores, pollen, sperm and egg cells. It is contemplated that any cell from which a fertile plant may be regenerated is useful as a recipient cell. Callus may be initiated from tissue sources including, but not limited to, immature embryos, seedling apical meristems, microspores and the like. Cells capable of proliferating as callus are also recipient cells for genetic transformation. Practical transformation methods and materials for making transgenic plants of this invention, e.g. various media and recipient target cells, transformation of immature embryos and subsequent regeneration of fertile transgenic plants are disclosed in U.S. Pat. Nos. 6,194,636 and 6,232,526, which are incorporated herein by reference.

The seeds of transgenic plants can be harvested from fertile transgenic plants and be used to grow progeny generations of transformed plants of this invention including hybrid plants line for screening of plants having an enhanced agronomic trait. In addition to direct transformation of a plant with a recombinant DNA, transgenic plants can be prepared by crossing a first plant having a recombinant DNA with a second plant lacking the DNA. For example, recombinant DNA can be introduced into first plant line that is amenable to transformation to produce a transgenic plant which can be crossed with a second plant line to introgress the recombinant DNA into the second plant line. A transgenic plant with recombinant DNA providing an enhanced agronomic trait, e.g. enhanced yield, can be crossed with transgenic plant line having other recombinant DNA that confers another trait, e.g. herbicide resistance or pest resistance, to produce progeny plants having recombinant DNA that confers both traits. Typically, in such breeding for combining traits the transgenic plant donating the additional trait is a male line and the transgenic plant carrying the base traits is the female line. The progeny of this cross will segregate such that some of the plants will carry the DNA for both parental traits and some will carry DNA for one parental trait; such plants can be identified by markers associated with parental recombinant DNA Progeny plants carrying DNA for both parental traits can be crossed back into the female parent line multiple times, e.g. usually 6 to 8 generations, to produce a progeny plant with substantially the same genotype as one original transgenic parental line but for the recombinant DNA of the other transgenic parental line In the practice of transformation DNA is typically introduced into only a small percentage of target cells in any one transformation experiment. Marker genes are used to provide an efficient system for identification of those cells that are stably transformed by receiving and integrating a transgenic DNA construct into their genomes. Preferred marker genes provide selective markers which confer resistance to a selective agent, such as an antibiotic or herbicide. Any of the herbicides to which plants of this invention may be resistant are useful agents for selective markers. Potentially transformed cells are exposed to the selective agent. In the population of surviving cells will be those cells where, generally, the resistance-conferring gene is integrated and expressed at sufficient levels to permit cell survival. Cells may be tested further to confirm stable integration of the exogenous DNA. Commonly used selective marker genes include those conferring resistance to antibiotics such as kanamycin and paromomycin (nptII), hygromycin B (aph IV) and gentamycin (aac3 and aacC4) or resistance to herbicides such as glufosinate (bar or pat) and glyphosate (aroA or EPSPS). Examples of such selectable are illustrated in U.S. Pat. Nos. 5,550,318; 5,633,435; 5,780,708 and 6,118,047, all of which are incorporated herein by reference. Screenable markers which provide an ability to visually identify transformants can also be employed, e.g., a gene expressing a colored or fluorescent protein such as a luciferase or green fluorescent protein (GFP) or a gene expressing a beta-glucuronidase or uidA gene (GUS) for which various chromogenic substrates are known.

Cells that survive exposure to the selective agent, or cells that have been scored positive in a screening assay, may be cultured in regeneration media and allowed to mature into plants. Developing plantlets can be transferred to plant growth mix, and hardened off, e.g., in an environmentally controlled chamber at about 85% relative humidity, 600 ppm $CO_2$, and 25-250 microeinsteins $m^{-2}$ $s^{-1}$ of light, prior to transfer to a greenhouse or growth chamber for maturation. Plants are regenerated from about 6 weeks to 10 months after a transformant is identified, depending on the initial tissue. Plants may be pollinated using conventional plant breeding methods known to those of skill in the art and seed produced, e.g. self-pollination is commonly used with transgenic corn. The regenerated transformed plant or its progeny seed or plants can be tested for expression of the recombinant DNA and screened for the presence of enhanced agronomic trait.

Transgenic Plants and Seeds

Transgenic plant seed provided by this invention are grown to generate transgenic plants having an enhanced trait as compared to a control plant. Such seed for plants with enhanced agronomic trait is identified by screening transformed plants or progeny seed for enhanced trait. For efficiency a screening program is designed to evaluate multiple transgenic plants (events) comprising the recombinant DNA, e.g. multiple plants from 2 to 20 or more transgenic events.

Transgenic plants grown from transgenic seed provided herein demonstrate improved agronomic traits that contribute to increased yield or other trait that provides increased plant value, including, for example, improved seed quality. Of particular interest are plants having enhanced yield resulting from improved plant growth and development, stress tolerance, improved seed development, higher light response, improved flower development, or improved carbon and/or nitrogen metabolism Many transgenic events which survive to fertile transgenic plants that produce seeds and progeny plants will not exhibit an enhanced agronomic trait. Screening is necessary to identify the transgenic plant having enhanced agronomic traits from populations of plants transformed as described herein by evaluating the trait in a variety of assays to detect an enhanced agronomic trait. These assays also may take many forms, including but not limited to, analyses to detect changes in the chemical composition, biomass, physiological properties, morphology of the plant.

The following examples illustrate aspects of the invention.

Example 1

This example illustrates preparation of a transformation vector useful for inserting a recombinant DNA construct of this invention into a transgenic plant to practice a method of this invention.

The LKR/SDH gene encodes a pre-protein for lysine ketoglutarate reductase (LKR) and saccharopine dehydrogenase (SDH) which are enzymes in a lysine catabolic pathway. Suppression of LKR is manifest in modification, e.g. increase, of lysine content. Suppression of LKR is effected by expressing in a planta recombinant DNA construct that produces a stabilized anti-sense RNA transcribed from anti-sense-oriented LKR DNA and sense-oriented LKR DNA which forms a loop of anti-sense-oriented RNA.

A transformation vector is prepared comprising two transcription units between right and left borders from *Agrobacterium tumefaciens*. One transcription unit for a marker comprised:
  (a) DNA of a rice actin promoter and rice actin intron,
  (b) DNA of a chloroplast transit peptide from *Arabidopsis* EPSPS
  (c) DNA of *A. tumefaciens* aroA (a glyphosate-resistant marker), and
  (d) DNA of *A. tumefaciens* NOS terminator,
The other transcription unit for LKR gene suppression comprised:
  (a) DNA of *Zea mays* GLB1 promoter,
  (b) DNA of a *Zea mays* ADH1 intron,
  (c) Anti-sense-oriented DNA fragment of *Zea mays* LKR,
  (d) Sense-oriented DNA fragment of *Zea mays* LKR, and
  (e) DNA of *Zea mays* GLB1 terminator.
SEQ ID NO: 1 is DNA sequence of a transformation vector comprising the above-described marker and gene suppression elements. See Table 1 below for a description of the elements of the transformation vector contained within SEQ ID NO:1.

TABLE 1

| Bases of SEQ ID NO: 1 | Description of DNA segment |
| --- | --- |
| 1-357 | *A. tumefaciens* right border |
| 376-1774 | DNA of a rice actin promoter and rice actin intron |
| 1784-2011 | DNA of *A. tumefaciens* EPSPS chloroplast transit peptide |
| 2012-3379 | DNA of *A. tumefaciens* aroA (glyphosate-resistant marker) |
| 3395-3647 | DNA of *A. tumefaciens* NOS terminator |
| 3691-4686 | DNA of *Zea mays* Glb1 terminator |
| 4692-5145 | Sense-oriented DNA element from *Zea mays* LKR |
| 5152-6118 | Anti-sense-oriented DNA element from *Zea mays* LKR |
| 6123-6680 | DNA of a *Zea mays* ADH1 intron |
| 6687-8082 | DNA of *Zea mays* GLB1 promoter |
| 8149-8590 | *A. tumefaciens* left border |

Figure 2:
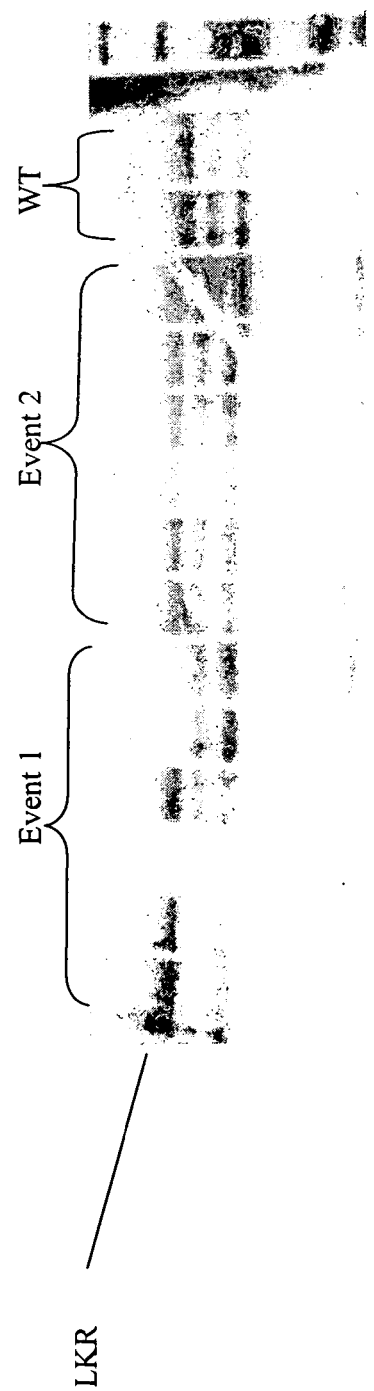
FIG. 2 is a Western analysis indicating gene suppression using a construct of this invention.

A vector prepared with the elements listed in Table 1 was used to transform corn plant tissue. Transgenic corn plants were obtained by *Agrobacterium*-mediated transformation. Transgenic plants from two separate transgenic insertion events were grown to produce F1 seed. Six mature seeds from each event were analyzed to determine success of transformation and suppression of LKR. The mature transgenic seeds were dissected to extract protein which was analyzed by Western analysis. With reference to FIG. 2, seed from one of the events showed no reduction in LKR as compared to wild type; and seed from the other event was shown to be segregating (1:1 hemizygous:wild type) as three of the six seeds showed substantial reduction in LKR as compared to wild type.

Example 2

This example illustrates a wide scope of embodiments of transformation vectors useful for inserting a recombinant DNA construct of this invention into a transgenic plant to practice a method of this invention. Transformation vectors were prepared using the following DNA elements where:
  (a) "pGcx" refers to DNA for a promoter derived from a gamma coixin gene from *Coix lacryma-jobi;*
  (b) "pZ27" refers to DNA for a promoter derived from a gamma zein gene from *Zea mays;*
  (c) "pZ27t" refers to DNA for a truncated promoter having 59 nucleotides leader sequence deleted from the 3' region of pZ27;

(d) "Z19as" refers to DNA for an antisense-oriented segment of 351 nucleotides from the coding sequence of a 19 kilo dalton alpha zein gene from *Zea mays;*

(e) "Z19s" refers to DNA for a sense-oriented segment of 351 nucleotides from the coding sequence of a 19 kilo dalton alpha zein gene from *Zea mays*, which is an inverted repeat of Z19as;

(f) "Z22as" refers to DNA for an antisense-oriented segment of 789 nucleotides from the coding sequence of a 22 kilo dalton alpha zein gene from *Zea mays;*

(g) "Z22asL" refers to DNA for an antisense-oriented segment of 785 nucleotides from the coding sequence of a 22 kilo dalton alpha zein gene from *Zea mays;*

(h) "Z22asSI" refers to DNA for an antisense-oriented segment of 789 nucleotides from the coding sequence of a 22 kilo dalton alpha zein gene from *Zea mays* having a 520 nucleotide long spliceable intron from a GB1 gene intron 3 from *Zea mays* inserted in the unpaired region;

(i) "Z22s" refers to DNA for a sense-oriented segment of 289 nucleotides from the coding sequence of a 22 kilo dalton alpha zein gene from *Zea mays*, which is an inverted repeat of the 5' end of Z22as; and (j) "TE9" refers to DNA for a sense oriented polyadenylation signal and site element from an RbcS2 gene from *Pisum sativum*.

With reference to Table 2 and SEQ ID NO:2 a transformation vector comprising "construct 2a" was made in the manner of Example 1 except that the transcription unit for LKR gene suppression was replaced by a transcription unit comprising the elements illustrated in the following schematic:

"Construct 2a" pZ27-Z19as-Z22asL-Z22s-Z19s-TE9

TABLE 2

| Bases of SEQ ID NO: 2 | description of DNA segment |
|---|---|
| 1-357 | *A. tumefaciens* right border |
| 376-1774 | DNA of a rice actin promoter and rice actin intron |
| 1784-2011 | DNA of *A. tumefaciens* EPSPS chloroplast transit peptide |
| 2012-3379 | DNA of *A. tumefaciens* aroA (glyphosate-resistant marker) |
| 3395-3647 | DNA of *A. tumefaciens* NOS terminator |
| 3479-4391 | DNA of *Pisum sativum* RbcS2 terminator |
| 4398-4748 | DNA for Z19s |
| 4755-5043 | DNA for Z22s |
| 5050-5835 | DNA of Z22asL |
| 5842-6192 | DNA of Z19as |
| 6204-7305 | DNA of *Zea mays* Z27 promoter |
| 7353-7794 | *A. tumefaciens* left border |

Corn callus was transformed and events with a single copy of the transformation vector were selected for growth into plants. Seed from plants grown from 26 of 29 single copy events showed substantial reduction of the 19 kilo dalton alpha zeins and the 22 kilo Dalton alpha zeins.

Other transformation vectors were made in a similar manner using the elements illustrated in the following Table 3.

TABLE 3

| Construct 2b1 | pGcx - Z19as - Z22asSI - Z22s - Z19s - TE9 |
| Construct 2b2* | pGcx - Z19as - Z22asSI - Z22s - Z19s - TE9 |
| Construct 2c | pZ27 - Z19as - Z22asSI - Z22s - Z19s - TE9 |
| Construct 2d | PZ27t - Z19as - Z22asSI - Z22s - Z19s - TE9 |
| Construct 2e | PZ27 - Z19as - Z22asL - Z19s - TE9 |

*construct 2b2 was inserted into a transformation vector that also included a transcription unit for expressing another gene having a promoter contiguous to pGcx.

Figure 3:
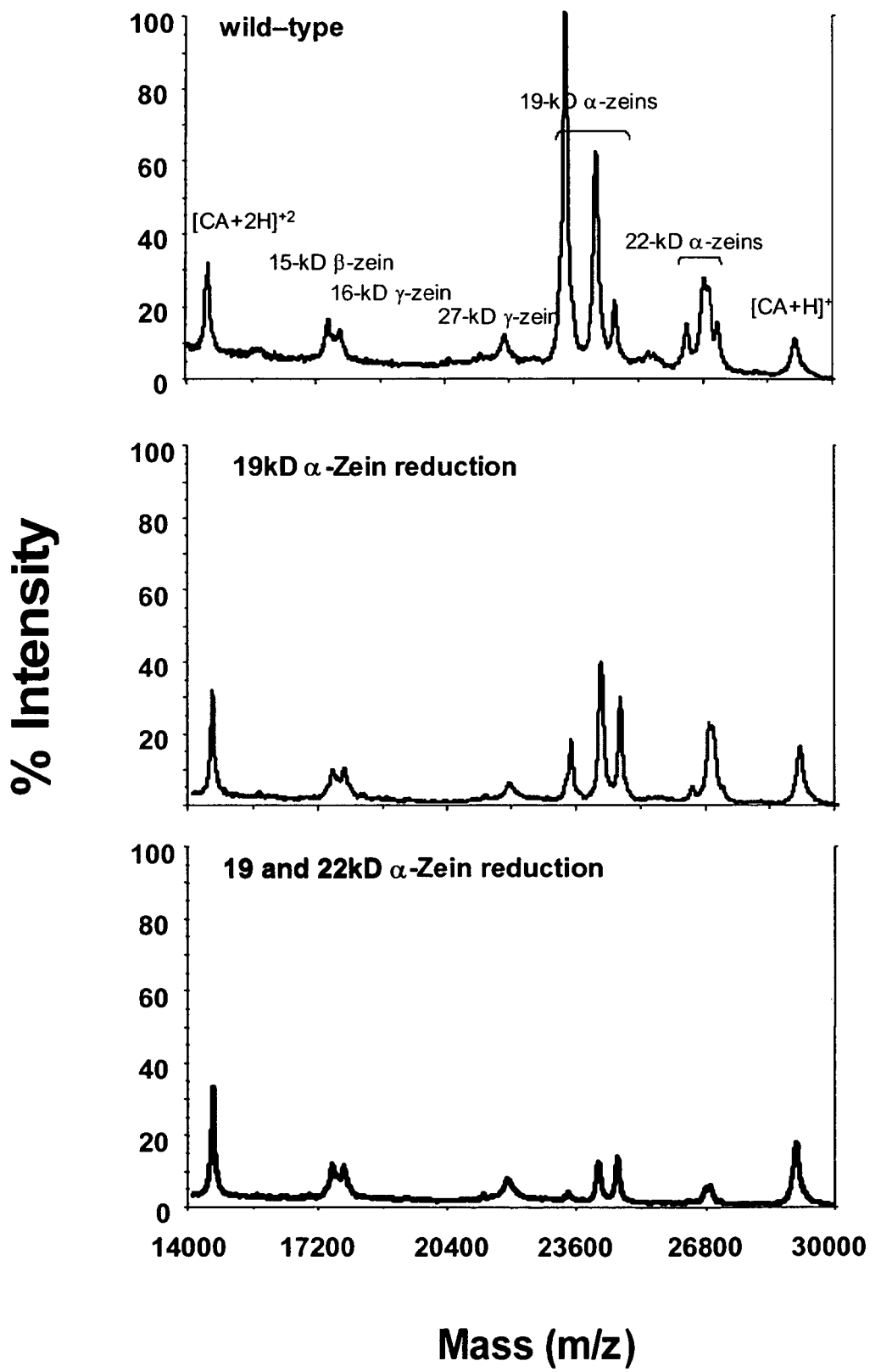
FIG. 3 shows mass spectroscopy spectra indicating zein content in seeds.

The efficiency of suppressing the alpha zeins in seeds produced by plants grown from single copy events is reported in Table 4 which reports the number of transgenic events with reduction of zeins as compared to the total number of transgenic events generated in each construct tested. The zein reduction phenotype is observed by MALDI-TOF MS (Matrix-Assisted-Laser-Desorption Ionization Time-Of-Flight Mass Spectrometry) analysis. FIG. 3 is illustrates typical spectra evidencing zein reduction.

TABLE 4

| Construct | 19 kD zein | 19 and 22 kD zein |
|---|---|---|
| 2a | 26/29 | 26/29 |
| 2b1 | 0/21 | 0/21 |
| 2b2 | 5/7 | 0/7 |
| 2c | 20/21 | 18/21 |
| 2d | 7/8 | 1/8 |
| 2e | 12/14 | 2/14 |

All of the materials and methods disclosed and claimed herein can be made and used without undue experimentation as instructed by the above disclosure. Although the materials and methods of this invention have been described in terms of preferred embodiments and illustrative examples, it will be apparent to those of skill in the art that variations may be applied to the materials and methods described herein without departing from the concept, spirit and scope of the invention. All such similar substitutes and modifications apparent to those skilled in the art are deemed to be within the spirit, scope and concept of the invention as defined by the appended claims.

What is claimed is:

1. A recombinant RNA molecule that forms a stabilized loop of single-stranded anti-sense-oriented RNA for suppressing at least one target gene, comprising in 5' to 3' order: an anti-sense-oriented RNA segment and a sense-oriented RNA segment;
   wherein the sense-oriented RNA segment is not more than about one-half the length of the anti-sense-oriented RNA segment, and the sense-oriented RNA segment is complementary to and forms a double-stranded segment with the 5'-most end of the anti-sense-oriented RNA segment, producing the stabilized loop of anti-sense-oriented RNA, further wherein the double-stranded segment has a minimum length of 21 nucleotides.

2. The recombinant RNA molecule of claim 1, wherein the at least one target gene is selected from the group consisting of: (a) a native plant gene; (b) an exogenous gene expressed in a plant; and (c) a gene of a plant pest.

3. The recombinant RNA molecule of claim 1, wherein the anti-sense-oriented RNA segment comprises segments from two or more genes targeted for suppression.

4. The recombinant RNA molecule of claim 1, wherein the sense-oriented RNA segment is from one gene targeted for suppression and the anti-sense-oriented RNA segments is from two or more genes targeted for suppression.

5. The recombinant RNA molecule of claim 1, wherein the sense-oriented RNA segment and the anti-sense-oriented RNA segment are from one gene targeted for suppression.

6. The recombinant RNA molecule of claim 1, wherein the loop of anti-sense-oriented RNA is closed with the segment of double-stranded RNA.

7. The recombinant RNA molecule of claim 6, wherein one strand of the segment of double-stranded RNA is identical to mRNA from a gene targeted for suppression.

8. The recombinant RNA molecule of claim 6, wherein one strand of the segment of double-stranded RNA is transcribed from DNA which is not from a gene targeted for suppression.

9. The recombinant RNA molecule of claim 1, wherein the sense-oriented RNA segment comprises from 50 to 500 nucleotides.

10. The recombinant RNA molecule of claim 1, wherein the sense-oriented RNA segment is not more than about one-third the length of the anti-sense-oriented RNA segment.

11. The recombinant RNA molecule of claim 1, wherein the sense-oriented RNA segment is not more than about one-quarter the length of the anti-sense-oriented RNA segment.

* * * * *

SEQUENCE LISTING

<160> NUMBER OF SEQ ID NOS: 2

<210> SEQ ID NO 1
<211> LENGTH: 8590
<212> TYPE: DNA
<213> ORGANISM: Artificial
<220> FEATURE:
<223> OTHER INFORMATION: recombinant DNA construct in plasmid between
      Agrabacterium borders

<400> SEQUENCE: 1 aggattttc ggcgctgcgc tacgtccgcg accgcgttga gggatcaagc cacagcagcc    60

-continued

```
cactcgacct tctagccgac ccagacgagc caagggatct ttttggaatg ctgctccgtc    120
gtcaggcttt ccgacgtttg ggtggttgaa cagaagtcat tatcgcacgg aatgccaagc    180
actcccgagg ggaaccctgt ggttggcatg cacatacaaa tggacgaacg gataaacctt    240
ttcacgccct tttaaatatc cgattattct aataaacgct cttttctctt aggtttaccc    300
gccaatatat cctgtcaaac actgatagtt taaactgaag gcgggaaacg acaatctgat    360
ccccatcaag cttactcgag gtcattcata tgcttgagaa gagagtcggg atagtccaaa    420
ataaaacaaa ggtaagatta cctggtcaaa agtgaaaaca tcagttaaaa ggtggtataa    480
agtaaaatat cggtaataaa aggtggccca aagtgaaatt tactcttttc tactattata    540
aaaattgagg atgttttgt cggtactttg atacgtcatt tttgtatgaa ttggttttta    600
agtttattcg cttttggaaa tgcatatctg tatttgagtc gggttttaag ttcgtttgct    660
tttgtaaata cagagggatt tgtataagaa atatctttag aaaaacccat atgctaattt    720
gacataattt ttgagaaaaa tatatattca ggcgaattct cacaatgaac aataataaga    780
ttaaaatagc tttcccccgt tgcagcgcat gggtattttt tctagtaaaa ataaaagata    840
aacttagact caaaacattt acaaaaacaa cccctaaagt tcctaaagcc caagtgcta    900 tccacgatcc atagcaagcc cagcccaacc caacccaacc cagcccaccc cagtccagcc    960
aactggacaa tagtctccac acccccccac tatcaccgtg agttgtccgc acgcaccgca   1020
cgtctcgcag ccaaaaaaaa aagaaagaaa aaaaagaaa aagaaaaaac agcaggtggg   1080
tccgggtcgt gggggccgga aacgcgagga ggatcgcgag ccagcgacga ggccggccct   1140
ccctccgctt ccaaagaaac gccccccatc gccactatat acatacccccc cctctcctc   1200 ccatccccccc aaccctacca ccaccaccac caccacctcc acctcctccc cctcgctgc   1260 cggacgacga gctcctcccc cctccccctc cgccgccgcc gcgccggtaa ccaccccgcc   1320
cctctcctct ttcttctcc gttttttttt ccgtctcggt ctcgatcttt ggccttggta   1380
gtttgggtgg gcgagaggcg gcttcgtgcg cgcccagatc ggtgcgcggg aggggcggga   1440
tctcgcggct ggggctctcg ccggcgtgga tccggcccgg atctcgcggg gaatggggct   1500
ctcggatgta gatctgcgat ccgccgttgt tgggggagat gatgggggt ttaaaatttc   1560 cgccgtgcta aacaagatca ggaagagggg aaaagggcac tatggtttat attttttatat   1620 atttctgctg cttcgtcagg cttagatgtg ctagatcttt cttttcttctt tttgtgggta   1680 gaatttgaat ccctcagcat tgttcatcgg tagtttttct tttcatgatt tgtgacaaat   1740
gcagcctcgt gcggagcttt tttgtaggta gaagtgatca accatggcgc aagttagcag   1800
aatctgcaat ggtgtgcaga acccatctct tatctccaat ctctcgaaat ccagtcaacg   1860
caaatctccc ttatcggttt ctctgaagac gcagcagcat ccacgagctt atccgatttc   1920
gtcgtcgtgg ggattgaaga agagtgggat gacgttaatt ggctctgagc ttcgtcctct   1980
taaggtcatg tcttctgttt ccacggcgtg catgcttcac ggtgcaagca gccggcccgc   2040
aaccgcccgc aaatcctctg gcctttccgg aaccgtccgc attcccggcg acaagtcgat   2100
ctcccaccgg tccttcatgt tcggcggtct cgcgagcggt gaaacgcgca tcaccggcct   2160
tctggaaggc gaggacgtca tcaatacggg caaggccatg caggcgatgg gcgcccgcat   2220
ccgtaaggaa ggcgacacct ggatcatcga tggcgtcggc aatggcggcc tcctggcgcc   2280
tgaggcgccg ctcgatttcg gcaatgccgc cacgggctgc cgcctgacga tgggcctcgt   2340
cggggtctac gatttcgaca gcaccttcat cggcgacgcc tcgctcacaa agcgcccgat   2400
gggccgcgtg ttgaacccgc tgcgcgaaat gggcgtgcag gtgaaatcgg aagacggtga   2460
```

-continued

```
ccgtcttccc gttaccttgc gcgggccgaa gacgccgacg ccgatcacct accgcgtgcc   2520
gatggcctcc gcacaggtga agtccgccgt gctgctcgcc ggcctcaaca cgcccggcat   2580
cacgacggtc atcgagccga tcatgacgcg cgatcatacg gaaagatgc tgcagggctt    2640 tggcgccaac cttaccgtcg agacggatgc ggacggcgtg cgcaccatcc gcctggaagg   2700
ccgcggcaag ctcaccggcc aagtcatcga cgtgccgggc gacccgtcct cgacggcctt   2760
cccgctggtt gcgccctgc ttgttccggg ctccgacgtc accatcctca acgtgctgat    2820
gaaccccacc cgcaccggcc tcatcctgac gctgcaggaa atgggcgccg acatcgaagt   2880
catcaacccg cgccttgccg gcggcgaaga cgtggcggac ctgcgcgttc gctcctccac   2940
gctgaagggc gtcacggtgc cggaagaccg cgcgccttcg atgatcgacg aatatccgat   3000
tctcgctgtc gccgccgcct tcgcggaagg ggcgaccgtg atgaacggtc tggaagaact   3060
ccgcgtcaag gaaagcgacc gcctctcggc cgtcgccaat ggcctcaagc tcaatggcgt   3120
ggattgcgat gagggcgaga cgtcgctcgt cgtgcgtggc cgccctgacg gcaaggggct   3180
cggcaacgcc tcgggcgccg ccgtcgccac ccatctcgat caccgcatcg ccatgagctt   3240
cctcgtcatg ggcctcgtgt cggaaaaccc tgtcacggtg gacgatgcca cgatgatcgc   3300
cacgagcttc ccggagttca tggacctgat ggccgggctg ggcgcgaaga tcgaactctc   3360
cgatacgaag gctgcctgat gagctcgaat tcccgatcgt tcaaacattt ggcaataaag   3420
tttcttaaga ttgaatcctg ttgccggtct tgcgatgatt atcatataat ttctgttgaa   3480
ttacgttaag catgtaataa ttaacatgta atgcatgacg ttatttatga gatgggtttt   3540
tatgattaga gtcccgcaat tatacattta atacgcgata gaaaacaaaa tatagcgcgc   3600
aaactaggat aaattatcgc gcgcggtgtc atctatgtta ctagatcggg gatgggggat   3660
ccactagtga tatccgtcga gtggcggccg cgttttatga ataataataa tgcatatctg   3720
tgcattacta cctgggatac aagggcttct ccgccataac aaattgagtt gcgatgctga   3780
gaacgaacgg ggaagaaagt aagcgccgcc caaaaaaaac gaacatgtac gtcggctata   3840
gcaggtgaaa gttcgtgcgc caatgaaaag ggaacgatat gcgttgggta gttgggatac   3900
ttaaatttgg agagtttgtt gcatacacta atccactaaa gttgtctatc tttttaacag   3960
ctctaggcag gatataagat ttatatctaa tctgttggag ttgcttttag agtaacttt    4020 ctctctgttt cgtttatagc cgattagcac aaaattaaac taggtgacga gaaataaaga   4080
aaaacggagg cagtaaaaaa tacccaaaaa aatacttgga gattttgtc tcaaaattat     4140 cttctaattt taaaagctac atattaaaaa tactatatat taaaaatact tcgagatcat   4200
tgcttgggat gggcagggcc aatagctaat tgctaaggat gggctatatt tatgtatcgt   4260
ctgaaacatg tagggctaa tagttagatg actaatttgc tgtgttcgta cggggtgctg    4320
tttgagccta gcgatgaagg gtcatagttt catacaagaa ctcactttg gttcgtctgc    4380 tgtgtctgtt ctcagcgtaa cggcatcaat ggatgccaaa ctccgcaagg ggacaaatga   4440
agaagcgaag agattataga acacgcacgt gtcattattt atttatggac ttgcctcagt   4500
agcttacagc atcgtacccg cacgtacata ctacagagcc acacttattg cactgcctgc   4560
cgcttacgta catagttaac acgcagagag gtatatacat acacgtccaa cgtctccact   4620
caggctcatg ctacgtacgc acgtcggtcg cgcgccaccc tctcgttgct tcctgctcgt   4680
tttggcgaat tccgatttgg caagtgttcc agagcaaaag ctggaagctc tcgtagtctg   4740
agcctctttg ctgattcata caagttatga ccatctacat ggatcgtctc accaagaaat   4800
```

```
ttgtagactg caggattttt ccctgaccgg agtgcaccag ctgggttcca actgaattta   4860
taggcaagcg gattgtttgc tgcagctgga gatggcaatc caccacagta agatgtaaat   4920
gcctttattt ttcccttcg tgcatgagct tcatcaatca tcttcattga catcaagtga    4980
tctatgccag gatctaggcc catttcacaa agtatagtta cacctgcatc tttggcagct   5040
tggctcaagt ttgacatgga ttcatcaaca tagcttgccg ttaccatgtg cttcttcaac   5100
tctatgcata ctcctgcaat ggcagcatga aaactagcag gcagcaccgg ttggacatca   5160
ttgagacagc tggaggttca tttcacttgg ttagatgtga agttggacaa agcacggatg   5220
atatgtcgta ctcagagctt gaagtaggag cagatgatac tgccacattg gataaaatta   5280
ttgattcctt gacttcttta gctaatgaac atggtggaga tcacgatgcc gggcaagaaa   5340
ttgaattagc tctgaagata ggaaaagtca atgagtatga aactgacgtc acaattgata   5400
aaggagggcc aaagatttta attcttggag ctggaagagt ctgtcggcca gctgctgagt   5460
ttctggcatc ttacccagac atatgtacct atggtgttga tgaccatgat gcagatcaaa   5520
ttcatgttat cgtggcatct ttgtatcaaa aagatgcaga agagacagtt gatggtattg   5580
aaaatacaac tgctacccag cttgatgttg ctgatattgg aagccttca gatcttgttt     5640 ctcaggttga ggttgtaatt agcttgctgc ctgctagttt tcatgctgcc attgcaggag   5700
tatgcataga gttgaagaag cacatggtaa cggcaagcta tgttgatgaa tccatgtcaa   5760
acttgagcca agctgccaaa gatgcaggtg taactatact ttgtgaaatg ggcctagatc   5820
ctggcataga tcacttgatg tcaatgaaga tgattgatga agctcatgca cgaaagggaa   5880
aaataaaggc atttacatct tactgtggtg gattgccatc tccagctgca gcaaacaatc   5940
cgcttgccta taaattcagt tggaacccag ctggtgcact ccggtcaggg aaaaatcctg   6000
cagtctacaa atttcttggt gagacgatcc atgtagatgg tcataacttg tatgaatcag   6060
caaagaggct cagactacga gagcttccag cttttgctct ggaacacttg ccaaatcggg   6120
atccgcagct gcacgggtcc aggaaagcaa tcgcatagtc aagctaaatc atcaagatgc   6180
aaacttttcg cccttgctaa acacggtaaa attcgaatgg acatgtgtgg agcagcaaag   6240
gccttacgtc cgagaaacag ggccactcaa cgagttagtt aaattcaaag aaagaaacgc   6300
ctccttgcaa gttgcaacat tcttagatca tactgatgaa aatgacgtct ttcattaaag   6360
aacagggaag atagatcttt gctcaatatc gtatgatgtg ttcagccaga ctgtcggatg   6420
gaccacacgg taatagcagt gctggacgat gttacatcga gaaagattac tagccttttc   6480
atgggagtga aggatataaa agaaataagt tcaccacgat tgcaggatag catacaagat   6540
cagcgccact gcggcactgt tcatcgaaaa aaaaactgtg gacgaagcta gctttcccca   6600
aaattactca acgaatcata aaccaagatt agtcagatca agacagagag gagaaacaag   6660
gcggaccttt gcacttgatc ggatccttgg gttggctgta tgcagaacta aagcggaggt   6720
ggcgcgcatt tataccagcg ccgggccctg gtacgtggcg cggccgcgcg gctacgtgga   6780
ggaaggctgc gtggcagcag acacacgggt cgccacgtcc cgccgtactc tccttaccgt   6840
gcttatccgg gctccggctc ggtgcacgcc agggtgtggc cgcctctgag cagactttgt   6900
cgtgttccac agtggtgtcg tgttccgggg actccgatcc gcggcgagcg accgagcgtg   6960
taaaagagtt cctactaggt acgttcattg tatctggacg acgggcagcg acaatttgc    7020 tgtaagagag gggcagtttt tttttagaaa aacagagaat tccgttgagc taattgtaat   7080
tcaacaaata agctattagt tggttttagc ttagattaaa gaagctaacg actaatagct   7140
aataattagt tggtctatta gttgactcat tttaaggccc tgtttcaatc tcgcgagata   7200
```

```
aactttagca gctattttt agctactttt agccatttgt aatctaaaca ggagagctaa    7260
tggtggtaat tgaaactaaa ctttagcact tcaattcata tagctaaagt ttagcaggaa    7320
gctaaacttt atcccgtgag attgaaacgg ggcctaaatc tctcagctat ttttgatgca    7380
aattactgtc actactggaa tcgagcgctt tgccgagtgt caaagcctga aaaacactcc    7440
gtaaagactt tgcctagtgt gacactcgac aaagagatct cgacgaacag tacatcgaca    7500
acggcttctt tgtcgagtac tttttatcgg acacttgaca aagtcttgt cgagtgaact     7560 acattgaaac tctatgattt tatgtgtagg tcacttaggt ttctacacat agtacgtcac    7620
aactttaccg aaacattatc aaattttat cacaacctct atatgata tcatgacatg       7680 tggacaagtt tcattaattt ctgactttat ttgtgtttta tacaatttt aaacaactag     7740 ataacaagtt cacggtcatg tttagtgagc atggtgcttg aagattctgg tctgcttctg    7800
aaatcggtcg taacttgtgc tagataacat gcatatcatt tattttgcat gcacggtttt    7860
ccatgtttcg agtgacttgc agtttaaatg tgaattttcc gaagaaattc aaataaacga    7920
actaaatcta atatttatag aaaacatttt tgtaaatatg taattgtgcc aaaatggtac    7980
atgtagatct acatagtgta ggaacatacc acaaaaagtt tggttggcaa aataaaaaaa    8040
ataaaatata ctttatccga gtgtccaagg tatggcactc ggcccgggtg gccaagctta    8100
ctagcccggg gcgcgcttaa ttaagcggcc gcatcgatcg tgaagtttct catctaagcc    8160
cccatttgga cgtgaatgta gacacgtcga ataaagatt tccgaattag aataatttgt    8220
ttattgcttt cgcctataaa tacgacggat cgtaatttgt cgttttatca aaatgtactt    8280
tcattttata ataacgctgc ggacatctac attttgaat tgaaaaaaaa ttggtaatta    8340
ctcttctttt ttctccatat tgaccatcat actcattgct gatccatgta gatttcccgg    8400
acatgaagcc atttacaatt gaatatatcc tgccgccgct gccgctttgc acccggtgga    8460
gcttgcatgt tggtttctac gcagaactga gccggttagg cagataattt ccattgagaa    8520
ctgagccatg tgcaccttcc ccccaacacg gtgagcgacg gggcaacgga gtgatccaca    8580
tgggactttt                                                          8590
```

<210> SEQ ID NO 2
<211> LENGTH: 7794
<212> TYPE: DNA
<213> ORGANISM: Artificial
<220> FEATURE:
<223> OTHER INFORMATION: recombinant DNA construct in plasmid between
      Agrobacterium borders

<400> SEQUENCE: 2

```
aggatttttc ggcgctgcgc tacgtccgcg accgcgttga gggatcaagc cacagcagcc      60
cactcgacct tctagccgac ccagacgagc caagggatct ttttggaatg ctgctccgtc     120
gtcaggcttt ccgacgtttg ggtggttgaa cagaagtcat tatcgcacgg aatgccaagc     180
actcccgagg ggaaccctgt ggttggcatg cacatacaaa tggacgaacg gataaacctt     240
ttcacgccct tttaaatatc gattattct aataaacgct ctttctctt aggtttaccc       300 gccaatatat cctgtcaaac actgatagtt taaactgaag gcgggaaacg acaatctgat    360
ccccatcaag cttactcgag gtcattcata tgcttgagaa gagagtcggg atagtccaaa    420
ataaaacaaa ggtaagatta cctggtcaaa agtgaaaaca tcagttaaaa ggtggtataa    480
agtaaaatat cggtaataaa aggtggccca agtgaaattt tactctttc tactattata    540 aaaattgagg atgttttgt cggtactttg atacgtcatt tttgtatgaa ttggtttta     600
```

```
agtttattcg cttttggaaa tgcatatctg tatttgagtc gggttttaag ttcgtttgct    660
tttgtaaata cagagggatt tgtataagaa atatctttag aaaaacccat atgctaattt    720
gacataattt ttgagaaaaa tatatattca ggcgaattct cacaatgaac aataataaga    780
ttaaaatagc tttccccgt tgcagcgcat gggtattttt tctagtaaaa ataaaagata     840
aacttagact caaaacattt acaaaaacaa cccctaaagt tcctaaagcc caaagtgcta    900
tccacgatcc atagcaagcc cagcccaacc caacccaacc caacccaccc cagtccagcc    960
aactggacaa tagtctccac acccccccac tatcaccgtg agttgtccgc acgcaccgca    1020
cgtctcgcag ccaaaaaaaa aagaaagaa aaaaagaaa aagaaaaaac agcaggtggg     1080
tccgggtcgt gggggccgga aacgcgagga ggatcgcgag ccagcgacga ggccggccct   1140
ccctccgctt ccaaagaaac gccccccatc gccactatat acataccccc cctctcctc    1200 ccatccccc aaccctacca ccaccaccac caccacctcc acctcctccc cctcgctgc     1260 cggacgacga gctcctcccc cctcccctc cgccgccgcc cgccggtaa ccaccccgcc     1320 cctctcctct ttctttctcc gtttttttt ccgtctcggt ctcgatcttt ggccttggta    1380
gtttgggtgg gcgagaggcg gcttcgtgcg cgcccagatc ggtgcgcggg aggggcggga   1440
tctcgcggct ggggctctcg ccggcgtgga tccggcccgg atctcgcggg gaatggggct   1500
ctcggatgta gatctgcgat ccgccgttgt tgggggagat gatgggggt ttaaaatttc    1560 cgccgtgcta acaagatca ggaagagggg aaaagggcac tatggtttat attttatat    1620 atttctgctg cttcgtcagg cttagatgtg ctagatcttt ctttcttctt tttgtgggta   1680
gaatttgaat ccctcagcat tgttcatcgg tagtttttct tttcatgatt tgtgacaaat   1740
gcagcctcgt gcggagcttt tttgtaggta gaagtgatca accatggcgc aagttagcag   1800
aatctgcaat ggtgtgcaga acccatctct tatctccaat ctctcgaaat ccagtcaacg   1860
caaatctccc ttatcggttt ctctgaagac gcagcagcat ccacgagctt atccgatttc   1920
gtcgtcgtgg ggattgaaga agagtgggat gacgttaatt ggctctgagc ttcgtcctct   1980
taaggtcatg tcttctgttt ccacggcgtg catgcttcac ggtgcaagca gccgccccgc   2040
aaccgcccgc aaatcctctg gcctttccgg aaccgtccgc attcccggcg acaagtcgat   2100
ctcccaccgg tccttcatgt tcggcggtct cgcgagcggt gaaacgcgca tcaccggcct   2160
tctggaaggc gaggacgtca tcaatacggg caaggccatg caggcgatgg gcgcccgcat   2220
ccgtaaggaa ggcgacacct ggatcatcga tggcgtcggc aatggcggcc tcctggcgcc   2280
tgaggcgccc ctcgatttcg gcaatgccgc cacgggctgc cgcctgacga tgggcctcgt   2340
cggggtctac gatttcgaca gcaccttcat cggcgacgcc tcgctcacaa agcgcccgat   2400
gggccgcgtg ttgaacccgc tgcgcgaaat gggcgtgcag gtgaaatcgg aagacggtga   2460
ccgtcttccc gttaccttgc gcgggccgaa gacgccgacg ccgatcacct accgcgtgcc   2520
gatggcctcc gcacaggtga agtccgccgt gctgctcgcc ggcctcaaca cgcccggcat   2580
cacgacggtc atcgagccga tcatgacgcg cgatcatacg gaaaagatgc tgcagggctt   2640
tggcgccaac cttaccgtcg agacggatgc ggacggcgtg cgcaccatcc gcctggaagg   2700
ccgcggcaag ctcaccggcc aagtcatcga cgtgccgggc gacccgtcct cgacggcctt   2760
cccgctggtt gcggccctgc ttgttccggg ctccgacgtc accatcctca acgtgctgat   2820
gaaccccacc cgcaccggcc tcatcctgac gctgcaggaa atgggcgccg acatcgaagt   2880
catcaacccg cgccttgccg gcggcgaaga cgtggcggac ctgcgcgttc gctcctccac   2940
```

```
gctgaagggc gtcacggtgc cggaagaccg cgcgccttcg atgatcgacg aatatccgat    3000
tctcgctgtc gccgccgcct tcgcggaagg ggcgaccgtg atgaacggtc tggaagaact    3060
ccgcgtcaag gaaagcgacc gcctctcggc cgtcgccaat ggcctcaagc tcaatggcgt    3120
ggattgcgat gagggcgaga cgtcgctcgt cgtgcgtggc cgccctgacg gcaaggggct    3180
cggcaacgcc tcgggcgccg ccgtcgccac ccatctcgat caccgcatcg ccatgagctt    3240
cctcgtcatg ggcctcgtgt cggaaaaccc tgtcacggtg gacgatgcca cgatgatcgc    3300
cacgagcttc ccggagttca tggacctgat ggccgggctg ggcgcgaaga tcgaactctc    3360
cgatacgaag gctgcctgat gagctcgaat tcccgatcgt tcaaacattt ggcaataaag    3420
tttcttaaga ttgaatcctg ttgccggtct tgcgatgatt atcatataat ttctgttgaa    3480
ttacgttaag catgtaataa ttaacatgta atgcatgacg ttatttatga gatgggtttt    3540
tatgattaga gtcccgcaat tatacattta atacgcgata gaaaacaaaa tatagcgcgc    3600
aaactaggat aaattatcgc gcgcggtgtc atctatgtta ctagatcggg gatgggggat    3660
ccactagtga tatccgtcga ctggtaccta cgcgtagcta gcccgggcgc gccttaatta    3720
agcggccgct tcgagtggct gcaggtcgat tgatgcatgt tgtcaatcaa ttggcaagtc    3780
ataaaatgca ttaaaaaata ttttcatact caactacaaa tccatgagta aactataat    3840 tataaagcaa tgattagaat ctgacaagga ttctggaaaa ttacataaag gaaagttcat    3900
aaatgtctaa aacacaagag gacatacttg tattcagtaa catttgcagc ttttctaggt    3960
ctgaaaatat atttgttgcc tagtgaataa gcataatggt acaactacaa gtgttttact    4020
cctcatatta acttcggtca ttagaggcca cgatttgaca cattttact caaaacaaaa    4080 tgtttgcata tctcttataa tttcaaattc aacacacaac aaataagaga aaaacaaat    4140 aatattaatt tgagaatgaa caaaaggacc atatcattca ttaactcttc tccatccatt    4200
tccatttcac agttcgatag cgaaaaccga ataaaaaaca cagtaaatta caagcacaac    4260
aaatggtaca agaaaaacag ttttcccaat gccataatac tcaaactcag taggattctg    4320
gtgtgtgcgc aatgaaactg atgcattgaa cttgacgaac gttgtcgaaa ccgatgatac    4380
gaacgaaagc tgaattccta gctggctgaa tggtagtagt tgttgctgct gtaaataagc    4440
aggagagttc aatgctgtca gttggttgaa tggaagaaat tgctgggggt aggcagcaga    4500
tagctggctg aatggtagtt gttgttgttg caaataagaa gcagagttca atgcagctag    4560
ttggttgaat ggaagaaact gctgttgctg agagtaggca gcaaggtttg ctagcacaag    4620
ttgttgtagt tgttgtgccc tgatgttttg tgccaataaa tgcaccaaag gtaactgctg    4680
taatagggct gatgattgtt ggaggaacaa gggtgataaa ggtaagatgc cagctgcgat    4740
tgcctgttat gcataaagat ggcacctcca acgatgggtt gctgcaaggc agggttcatc    4800
aaagagaact ggttgtatgg cagcaattgt tgttgctgct gcaggaaggt agcgaccaat    4860
gggttagcca ctgccaatgg attaagtaac tgttgtcgct gttgtaggta cgcagcagag    4920
tttgacacag ccagttggtt gaatggaagc aactgttgta agtaggcagc agggtttgcc    4980
acagctagct gagtcagagc tggtacaatt tgttgcagca actgttgttg taggtacgta    5040
ggtgggcccg ctaccaagat attagccctc cttgcgcttc ttgcccttt agtgagcgca    5100 acaaatgcgt tcattattcc acagtgctca cttgctccta gtgccagtat tccacagttc    5160
ctcccaccag ttacttcaat gggcttcgaa catccagccg tgcaagccta caggctacaa    5220
ctagcgcttg cggcgagcgc cttacaacaa ccaattgccc aattgcaaca acaatccttg    5280
gcacatctaa ccctacaaac cattgcaacg caacaacaac aacaacagtt tctgccatca    5340
```

```
ctgagccacc tagccgtggt gaaccctgtc acctacttgc aacagcagct gcttgcatcc    5400
aacccacttg ctctggcgaa cgtagctgca taccagcaac aacaacagct gcaacagttt    5460
atgccagtgc tcagtcaact agccatggtg aaccctgccg tctacctaca actactttca    5520
tctagcccgc tcgcggtggg caatgcacct acgtacctac aacaacagtt gctgcaacaa    5580
attgtaccag ctctgactca gctagctgtg gcaaaccctg ctgcctactt acaacagttg    5640
cttccattca accaactggc tgtgtcaaac tctgctgcgt acctacaaca gcgacaacag    5700
ttacttaatc cattggcagt ggctaaccca ttggtcgcta ccttcctgca gcagcaacaa    5760
caattgctgc catacaacca gttctctttg atgaaccctg ccttgcagca acccatcgtt    5820
ggaggtgcca tctttaccgg taacaggcaa tcgcagctgg catcttacct ttatcaccct    5880
tgttcctcca acaatcatca gcccattaca agcagttacc tttggtgcat ttattggcac    5940
aaaacatcag gcacaacaa ctacaacaac ttgtgctagc aaaccttgct gcctactctc    6000
agcaacaaca gtttcttcca ttcaaccaac tagctgcatt gaactctgct tcttatttgc    6060
aacaacaaca actaccattc agccagctat ctgctgccta cccccagcaa tttcttccat    6120
tcaaccaact gacagctttg aactctcctg cttatttaca gcagcaacaa ctactaccat    6180
tcagccagct agggatccgg taccgggttc ttctgcgctc tggagtagat aaagctaatg    6240
gtctgaagac ccagtggtgg tgatggagaa gtgcacaggc atgcgagcgt tatttatagc    6300
tttgattaat taacacaatt tcttgtgttc ttatgccacc gagacggctg taggcagctt    6360
catggtttct tgccaaatgt atatgactcg tcactctctt tacgtagcac gtcgatggtt    6420
catctggaat cattctgtac ttctgcgtgg ctcagttttg ttgccttcta caggttgttg    6480
atctacgtaa aacgaattag atttagcttg acatatggct ttttttttgt tgtaaattta    6540
ctttacacgt caaggatttt tgtcctgtcc ggcctatttt atttttcatg aaacgatctt    6600
tgtaatgcaa tatgagttgt ttgtaatgtc ttgtgagctg taagcatgta tatcagatga    6660
gtatgatctc ggcatgactc accgtgtttc tttgcacaca gagaggattt gtttgattgt    6720
ttcttaccca ataccttga cgtgcaattt tggttgatgt tctgtgagtt gttaaggata    6780
caacaaattc ttggagcttt acatgccaat gcatggttgt ttcgtgttcc tcaccacttt    6840
aggacttata cggttgcacc tggatgatcg aagggattg ggagagatta aatctccttc    6900
tattcaattt tgactaggaa gagatttaat cgtttccaac ccctttcgat ccagacgtaa    6960
gcgaacaagt tttttatttg gataccctct tattcatctt aatacacaca tgtattaagt    7020
tgcactagtt atatgcccgt gcattgctac ggtttatata tatatatata tatatgtata    7080
tatatatata tgatatatga taaattttgt tttaataaaa catatgtttt ctattgatta    7140
ggttgtgtga atatggagcc aacaaccaat atccagaaca cttatacata atttcacctt    7200
attttgtaca taaactctct tattatagta gtagagaaga gattataaga gtgcgggttg    7260
attataaaga aatgtaggag ttttttaata atattgacgc gggacaagct tactagtagc    7320
ttgttaacgc ggccgcatcg atcgtgaagt ttctcatcta agcccccatt tggacgtgaa    7380
tgtagacacg tcgaaataaa gatttccgaa ttagaataat tgttttattg ctttcgccta    7440
taaatacgac ggatcgtaat ttgtcgtttt atcaaaatgt actttcattt tataataacg    7500
ctgcggacat ctacattttt gaattgaaaa aaaattggta attactcttt cttttctcc    7560 atattgacca tcatactcat tgctgatcca tgtagatttc ccggacatga agccatttac    7620
aattgaatat atcctgccgc cgctgccgct ttgcacccgg tggagcttgc atgttggttt    7680
```

```
ctacgcagaa ctgagccggt taggcagata atttccattg agaactgagc catgtgcacc    7740 ttcccccaa cacggtgagc gacggggcaa cggagtgatc cacatgggac tttt           7794
```